(12) United States Patent
Skranc et al.

(10) Patent No.: US 7,572,608 B2
(45) Date of Patent: Aug. 11, 2009

(54) R-HYDROXYNITRILLYASES HAVING IMPROVED SUBSTRATE TOLERANCE AND THE USE THEREOF

(75) Inventors: Wolfgang Skranc, Vienna (AT); Anton Glieder, Gleisdorf (AT); Karl Gruber, Graz (AT); Roland Weis, Graz (AT); Ruud Luiten, Leiden (NL)

(73) Assignee: DSM Fine Chemicals Austria NFG GmbH & Co. KG, Linz (AT)

( * ) Notice: Subject to any disclaimer, the term of this patent is extended or adjusted under 35 U.S.C. 154(b) by 0 days.

(21) Appl. No.: 10/548,271

(22) PCT Filed: Feb. 24, 2004

(86) PCT No.: PCT/EP2004/001778
§ 371 (c)(1), (2), (4) Date: Sep. 7, 2005

(87) PCT Pub. No.: WO2004/083424
PCT Pub. Date: Sep. 30, 2004

(65) Prior Publication Data
US 2006/0105434 A1    May 18, 2006

(30) Foreign Application Priority Data
Mar. 20, 2003    (AT) .............................. A 447/2003

(51) Int. Cl.
C12P 13/04    (2006.01)
C12N 9/88    (2006.01)

(52) U.S. Cl. ...................................... 435/128; 435/232

(58) Field of Classification Search ........................ None
See application file for complete search history.

(56) References Cited

U.S. PATENT DOCUMENTS 6,319,697 B1    11/2001    Effenbrger et al.

6,861,243 B2    3/2005    Schwab et al.

FOREIGN PATENT DOCUMENTS

| EP | 0 969 095 A2 | 1/2000 |
|----|--------------|--------|
| EP | 1 223 220 A1 | 7/2002 |

OTHER PUBLICATIONS

Glieder et al.(Angew. Chem.. Intl. ed. 2003, 42, 4815-4818).*
Glieder et al. (Ang chem. Intl ed. 42, 4815-4818, 2003), In IDS.*
Whisstock, et al. Quarterly Rev. Biophy. 2003, 36, pp. 307-340.*
Ingrid Dreveny et al, The active site of hydroxynitrile lyase from *Prunus amygdalus*: Modeling studies provide new insights into the mechanism of cyanogenesis; Feb. 2002, pp. 292-300, XP-002281486.
Ingrid Dreveny et al, The hydroxynitrile lyase from Almond: A Lyase that looks like an oxidoreductase; Sep. 2001; pp. 803-815; XP-002281487.
Herfried Griengl et al, The synthesis of chiral cyanohydrins by oxynitrilases; Jun. 2000; pp. 252-256; XP-002249789.
Anton Glieder et al, Comprehensive Step-by-Step Engineering of an (R)-Hydroxynitrile Lyase for Large-Scale Asymmetric Synthesis; Oct. 13, 2003; pp. 4815-4818; XP-002281488.

* cited by examiner

*Primary Examiner*—Nashaat T Nashed
*Assistant Examiner*—Md. Younus Meah
(74) *Attorney, Agent, or Firm*—Nixon & Vanderhye P.C.

(57) ABSTRACT

The invention relates to R-hydroxynitrillyases from the family of Rosaceae that are characterized by an improved substrate tolerance and increased stability. In the active center of the R-hydroxynitrillyases either a) an alanine group is substituted by glycine, valine, leucine, isoleucine, or phenylalanine or b) a phenylalanine group is substituted by alanine, glycine valine, leucine or isoleucine, or c) a leucine group is substituted by alanine, glycine, valine, isoleucine or phenylalanine, or d) an isoleucine group is substituted by alanine, glycine, valine, leucine or phenylalanine. The invention also relates to the use of these lyases in the production of enantiomer-pure R- or S-cyanohydrines.

9 Claims, 1 Drawing Sheet

The mutant PaHNL5 alpha_L1Q, A111G (A111G) showed very good stability at low pH compared with commercially available native PaHNL from almond kernels.

rA: relative activity in %
t/min: incubation time at pH 2.6 in minutes

```
                        SEQUENCE LISTING

<160> NUMBER OF SEQ ID NOS: 27

<210> SEQ ID NO 1
<211> LENGTH: 29
<212> TYPE: DNA
<213> ORGANISM: Artificial Sequence
<220> FEATURE:
<223> OTHER INFORMATION: primer for Prunus serotina

<400> SEQUENCE: 1
actacgaatt cgaccatgga gaaatcaac                                        29

<210> SEQ ID NO 2
<211> LENGTH: 33
<212> TYPE: DNA
<213> ORGANISM: Artificial Sequence
<220> FEATURE:
<223> OTHER INFORMATION: primer for Prunus serotina

<400> SEQUENCE: 2
cactggaatt caaagagcaa cacttatcca cgg                                   33

<210> SEQ ID NO 3
<211> LENGTH: 20
<212> TYPE: DNA
<213> ORGANISM: Artificial Sequence
<220> FEATURE:
<223> OTHER INFORMATION: primer for Prunus serotina

<400> SEQUENCE: 3
```

-continued

```
aagaggaaca cttagccacg                                            20

<210> SEQ ID NO 4
<211> LENGTH: 20
<212> TYPE: DNA
<213> ORGANISM: Artificial Sequence
<220> FEATURE:
<223> OTHER INFORMATION: primer for Prunus serotina

<400> SEQUENCE: 4
caacaatgtc cgctgtagtg                                            20

<210> SEQ ID NO 5
<211> LENGTH: 43
<212> TYPE: DNA
<213> ORGANISM: Artificial Sequence
<220> FEATURE:
<223> OTHER INFORMATION: primer

<400> SEQUENCE: 5
tcttcgaaga attcacgatg agatttcctt caatttttac tgc                  43

<210> SEQ ID NO 6
<211> LENGTH: 36
<212> TYPE: DNA
<213> ORGANISM: Artificial Sequence
<220> FEATURE:
<223> OTHER INFORMATION: primer

<400> SEQUENCE: 6
gaagtattgg caagagcttc agcctctctt ttctcg                          36

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
gaagtattgg cttgagcttc agcctctctt ttctcg                          36

<210> SEQ ID NO 8
<211> LENGTH: 37
<212> TYPE: DNA
<213> ORGANISM: Artificial Sequence
<220> FEATURE:
<223> OTHER INFORMATION: primer

<400> SEQUENCE: 8
agagaggctg aagctcttgc caatacttct gctcatg                         37

<210> SEQ ID NO 9
<211> LENGTH: 37
<212> TYPE: DNA
<213> ORGANISM: Artificial Sequence
<220> FEATURE:
<223> OTHER INFORMATION: primer

<400> SEQUENCE: 9
agagaggctg aagctcaagc caatacttct gctcatg                         37

<210> SEQ ID NO 10
<211> LENGTH: 43
<212> TYPE: DNA
```

<213> ORGANISM: Artificial Sequence
<220> FEATURE:
<223> OTHER INFORMATION: primer

<400> SEQUENCE: 10
atggtaccga attctcacat ggactcttga atattatgaa tag        43

<210> SEQ ID NO 11
<211> LENGTH: 44
<212> TYPE: DNA
<213> ORGANISM: Artificial Sequence
<220> FEATURE:
<223> OTHER INFORMATION: primer for site-specific mutagenesis

<400> SEQUENCE: 11
gtggcacgac cataatcaat ggaggcgtct acgccagagc taac        44

<210> SEQ ID NO 12
<211> LENGTH: 44
<212> TYPE: DNA
<213> ORGANISM: Artificial Sequence
<220> FEATURE:
<223> OTHER INFORMATION: primer for site-specific mutagenesis

<400> SEQUENCE: 12
gttagctctg gcgtagacgc ctccattgat tatggtcgtg ccac        44

<210> SEQ ID NO 13
<211> LENGTH: 41
<212> TYPE: DNA
<213> ORGANISM: Artificial Sequence
<220> FEATURE:
<223> OTHER INFORMATION: primer for site-specific mutagenesis

<400> SEQUENCE: 13
gcacgaccat aatcaatgct tgcgtctacg ccagagctaa c        41

<210> SEQ ID NO 14
<211> LENGTH: 44
<212> TYPE: DNA
<213> ORGANISM: Artificial Sequence
<220> FEATURE:
<223> OTHER INFORMATION: primer for site-specific mutagenesis

<400> SEQUENCE: 14
gttagctctg gcgtagacgc aagcattgat tatggtcgtg ccac        44

<210> SEQ ID NO 15
<211> LENGTH: 44
<212> TYPE: DNA
<213> ORGANISM: Artificial Sequence
<220> FEATURE:
<223> OTHER INFORMATION: primer for site-specific mutagenesis

<400> SEQUENCE: 15
gtggcacgac cataatcaat ggttgcgtct acgccagagc taac        44

<210> SEQ ID NO 16
<211> LENGTH: 44
<212> TYPE: DNA
<213> ORGANISM: Artificial Sequence
<220> FEATURE:
<223> OTHER INFORMATION: primer for site-specific mutagenesis

<400> SEQUENCE: 16
gttagctctg gcgtagacgc aaccattgat tatggtcgtg ccac        44

<210> SEQ ID NO 17
<211> LENGTH: 44
<212> TYPE: DNA
<213> ORGANISM: Artificial Sequence
<220> FEATURE:
<223> OTHER INFORMATION: primer for site-specific mutagenesis

<400> SEQUENCE: 17
tccaattgaa gcctctgttg saactgtttt aggcattaga agtg         44

<210> SEQ ID NO 18
<211> LENGTH: 44
<212> TYPE: DNA
<213> ORGANISM: Artificial Sequence
<220> FEATURE:
<223> OTHER INFORMATION: primer for site-specific mutagenesis

<400> SEQUENCE: 18
ctaatgccta aaacagttsc aacagaggct tcaattggat ttgg         44

<210> SEQ ID NO 19
<211> LENGTH: 44
<212> TYPE: DNA
<213> ORGANISM: Artificial Sequence
<220> FEATURE:
<223> OTHER INFORMATION: primer for site-specific mutagenesis

<400> SEQUENCE: 19
cacgttgact gcagatgggg ctgcatataa tctgcagcaa caag         44

<210> SEQ ID NO 20
<211> LENGTH: 44
<212> TYPE: DNA
<213> ORGANISM: Artificial Sequence
<220> FEATURE:
<223> OTHER INFORMATION: primer for site-specific mutagenesis

<400> SEQUENCE: 20
cttgttgctg cagattatat gcagccccat cagcagtcaa cgtg         44

<210> SEQ ID NO 21
<211> LENGTH: 43
<212> TYPE: DNA
<213> ORGANISM: Artificial Sequence
<220> FEATURE:
<223> OTHER INFORMATION: primer for site-specific mutagenesis

<400> SEQUENCE: 21
ccactccacc ctttaggctt ttcctacaac atcttacccc ctc         43

<210> SEQ ID NO 22
<211> LENGTH: 44
<212> TYPE: DNA
<213> ORGANISM: Artificial Sequence
<220> FEATURE:
<223> OTHER INFORMATION: primer for site-specific mutagenesis

<400> SEQUENCE: 22
aagatgttgt aggaaaagca ctaaagggtg gagtggaaaa tggc         44

<210> SEQ ID NO 23
<211> LENGTH: 44
<212> TYPE: DNA
<213> ORGANISM: Artificial Sequence
<220> FEATURE:

-continued

```
<223> OTHER INFORMATION: primer for site-specific mutagenesis

<400> SEQUENCE: 23
agtgattatt atcaagtttc tgcctcaagc ttgccatttt ccac                    44

<210> SEQ ID NO 24
<211> LENGTH: 44
<212> TYPE: DNA
<213> ORGANISM: Artificial Sequence
<220> FEATURE:
<223> OTHER INFORMATION: primer for site-specific mutagenesis

<400> SEQUENCE: 24
ggaaaatggc aagcttgagg cagaaacttg ataataatca cttc                    44

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
gcaaatggca ttctgacatc c                                             21

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
gactggttcc aattgacaag c                                             21

<210> SEQ ID NO 27
<211> LENGTH: 531
<212> TYPE: PRT
<213> ORGANISM: Artificial Sequence
<220> FEATURE:
<223> OTHER INFORMATION: mutant PaHNL5 A111G

<400> SEQUENCE: 27
```

Leu Ala Asn Thr Ser Ala His Asp Phe Ser Tyr Leu Lys Phe Val Tyr
1               5                   10                  15

Asn Ala Thr Asp Thr Ser Ser Glu Gly Ser Tyr Asp Tyr Ile Val Ile
            20                  25                  30

Gly Gly Gly Thr Ser Gly Cys Pro Leu Ala Ala Thr Leu Ser Glu Lys
        35                  40                  45

Tyr Lys Val Leu Leu Leu Glu Arg Gly Thr Ile Ala Thr Glu Tyr Pro
    50                  55                  60

Asn Thr Leu Thr Ala Asp Gly Phe Ala Tyr Asn Leu Gln Gln Gln Asp
65                  70                  75                  80

Asp Gly Lys Thr Pro Val Glu Arg Phe Val Ser Glu Asp Gly Ile Asp
                85                  90                  95

Asn Val Arg Ala Arg Ile Leu Gly Gly Thr Thr Ile Ile Asn Gly Gly
            100                 105                 110

Val Tyr Ala Arg Ala Asn Ile Ser Phe Tyr Ser Gln Thr Gly Ile Glu
        115                 120                 125

Trp Asp Leu Asp Leu Val Asn Lys Thr Tyr Glu Trp Val Glu Asp Ala
    130                 135                 140

-continued

```
Ile Val Val Lys Pro Asn Asn Gln Ser Trp Gln Ser Val Ile Gly Glu
145                 150                 155                 160

Gly Phe Leu Glu Ala Gly Ile Leu Pro Asp Asn Gly Phe Ser Leu Asp
                165                 170                 175

His Glu Ala Gly Thr Arg Leu Thr Gly Ser Thr Phe Asp Asn Asn Gly
            180                 185                 190

Thr Arg His Ala Ala Asp Glu Leu Leu Asn Lys Gly Asp Pro Asn Asn
        195                 200                 205

Leu Leu Val Ala Val Gln Ala Ser Val Glu Lys Ile Leu Phe Ser Ser
    210                 215                 220

Asn Thr Ser Asn Leu Ser Ala Ile Gly Val Ile Tyr Thr Asp Ser Asp
225                 230                 235                 240

Gly Asn Ser His Gln Ala Phe Val Arg Gly Asn Gly Glu Val Ile Val
                245                 250                 255

Ser Ala Gly Thr Ile Gly Thr Pro Gln Leu Leu Leu Leu Ser Gly Val
            260                 265                 270

Gly Pro Glu Ser Tyr Leu Ser Ser Leu Asn Ile Thr Val Val Gln Pro
        275                 280                 285

Asn Pro Tyr Val Gly Gln Phe Val Tyr Asp Asn Pro Arg Asn Phe Ile
    290                 295                 300

Asn Ile Leu Pro Pro Asn Pro Ile Glu Ala Ser Val Val Thr Val Leu
305                 310                 315                 320

Gly Ile Arg Ser Asp Tyr Tyr Gln Val Ser Leu Ser Ser Leu Pro Phe
                325                 330                 335

Ser Thr Pro Pro Phe Ser Leu Phe Pro Thr Thr Ser Tyr Pro Leu Pro
            340                 345                 350

Asn Ser Thr Phe Ala His Ile Val Ser Gln Val Pro Gly Pro Leu Ser
        355                 360                 365

His Gly Ser Val Thr Leu Asn Ser Ser Ser Asp Val Arg Ile Ala Pro
    370                 375                 380

Asn Ile Lys Phe Asn Tyr Tyr Ser Asn Ser Thr Asp Leu Ala Asn Cys
385                 390                 395                 400

Val Ser Gly Met Lys Lys Leu Gly Asp Leu Leu Arg Thr Lys Ala Leu
                405                 410                 415

Glu Pro Tyr Lys Arg Asp Val Leu Gly Ile Asp Gly Phe Asn Tyr Leu
            420                 425                 430

Gly Val Pro Leu Pro Glu Asn Gln Thr Asp Asp Ala Ser Phe Glu Thr
        435                 440                 445

Phe Cys Leu Asp Asn Val Ala Ser Tyr Trp His Tyr His Gly Gly Ser
    450                 455                 460

Leu Val Gly Lys Val Leu Asp Asp Ser Phe Arg Val Met Gly Ile Lys
465                 470                 475                 480

Ala Leu Arg Val Val Asp Ala Ser Thr Phe Pro Tyr Glu Pro Asn Ser
                485                 490                 495

His Pro Gln Gly Phe Tyr Leu Met Leu Gly Arg Tyr Val Gly Leu Gln
            500                 505                 510

Ile Leu Gln Glu Arg Ser Ile Arg Leu Glu Ala Ile His Asn Ile Gln
        515                 520                 525

Glu Ser Met
    530
```

R-HYDROXYNITRILLYASES HAVING IMPROVED SUBSTRATE TOLERANCE AND THE USE THEREOF

This application is the US national phase of international application PCT/EP2004/001778 filed 24 Feb. 2004 which designated the U.S. and claims benefit of AT A 447/2003, dated 20 Mar. 2003, the entire content of which is hereby incorporated by reference.

Biocatalytic processes have become very important for the chemical industry. The carrying-out of chemical reactions with the assistance of biological catalysts is in this connection of interest especially in areas of application in which it is possible to exploit the property of enzymes, which is often present, of preferentially converting or forming one of the two enantiomers in chemical reactions with chiral or pro-chiral components.

Essential preconditions for exploiting these favorable properties of enzymes are their availability in the quantities required industrially and a sufficiently high reactivity, as well as stability under the actual conditions of an industrial process.

A particularly interesting class of chiral chemical compounds are cyanohydrins. Cyanohydrins are important for example in the synthesis of α-hydroxy acids, α-hydroxy ketones, β-amino alcohols, which are used for obtaining biologically active substances, e.g. active pharmaceutical ingredients, vitamins or pyrethroid compounds.

These cyanohydrins are prepared by addition of hydrocyanic acid onto the carbonyl group of a ketone or aldehyde.

It has been possible to achieve the industrial preparation of chiral compounds such as, for example, (S)-cyanohydrins by making the enzyme (S)-hydroxynitrile lyase from *Hevea brasiliensis* available, as described for example in WO 97/03204, EP 0 951561 and EP 0 927 766.

However, there is a multiplicity of interesting chemical compounds for which the R enantiomers are important for industrial applications. To date, only processes for preparing a number of products which can be employed only on the laboratory scale have been described (e.g.: EP 0 276 375, EP 0 326 063, EP 0 547 655). The enzyme preparations employed in these cases were mainly those obtained from plants of the Rosaceae family, for example from almond kernels (*Prunus amygdalus*).

Further R-HNLs which have been employed to date are, for example, those from linseed seedlings (*Linum usitatissimum*; LUHNL) which were cloned as first gene of an R-HNL and were expressed in *E. Coli* and *Pichia pastoris*, or R-HNL from *Phlebodium aureurum*.

Industrial applications on a larger scale have not been achieved to date. The essential reason for this is that enzyme preparations from plants of the Rosaceae family having hydroxynitrile lyase (HNL) activity or those from linseed seedlings have not to date been available in sufficient quantities and at reasonable costs and, moreover, showed a stability which was too low at low pH values.

Advantageous reaction parameters described in the literature for obtaining products with high optical purity are low temperatures (e.g. Persson et al.; Enzyme and Microbial Technology 30(7), 916-923; 2002), a pH below 4 (e.g. Kragl et al.; Annals of the New York Academy of Science; 613 (enzyme Eng. 10), 167-75, 1990), and the use of 2-phase systems (for example EP 0 547 655) or of emulsions (e.g. EP 1 238 094). Unfortunately, most R-HNLs have half-lives of less than one hour at a pH below 4.

EP 1223220 A1 describes recombinant enzymes which are prepared by cloning a gene from *Prununs amygdalus*, which codes for an R-HNL isoenzyme, for example for isoenzyme 5 (PaHNL5), and by heterologous expression for example in *Pichia pastoris*, which are distinguished, as is evident from the examples, by a considerably increased stability at low pH values compared with the other known R-HNLs.

A disadvantage which has been found is that the substrate acceptance is unsatisfactory, because conversion of some substrates in the presence of, for example, recombinant PaHNL5 takes place at a distinctly lower reaction rate than in the presence of commercially available vegetable, native (R)-HNL preparations from almond kernels.

It was therefore an object of the invention to provide R-hydroxynitrile lyases from the Rosaceae family which firstly can be provided on a sufficient scale and cost-effectively for technical conversions on the industrial scale, and which display an improved substrate acceptance and an increased stability.

The invention accordingly relates to R-hydroxynitrile lyases from the Rosaceae family having improved substrate acceptance and increased stability, which are characterized in that in the active center of the R-hydroxynitrile lyases there is replacement either of a) an alanine residue by glycine, valine, leucine, isoleucine or phenylalanine or b) a phenylalanine residue by alanine, glycine, valine, leucine or isoleucine or c) a leucine residue by alanine, glycine, valine, isoleucine or phenylalanine or d) an isoleucine residue by alanine, glycine, valine, leucine or phenylalanine.

The R-HNLs of the invention are mutants of R-hydroxynitrile lyases from the Rosaceae family.

It is possible to employ as initial basis for preparing the mutants of the invention native R-HNLs from the Rosaceae family, such as, for example, R-HNLs from *Prunus amygdalys* (PaHNL), *Prunus serotina* (PsHNL), *Prunus laurocerasus, Prunus lyonii, Prunus armaniaca, Prunus persica, Prunus domestica* (PdHNL), *Malus communis*, etc. or recombinant R-HNLs, as disclosed for example in EP 1223220, and so-called tunnel mutants of the abovementioned R-HNLs, in which one or more bulky amino acid residues within the hydrophobic channel leading to the active center are replaced by less bulky amino acid residues.

The native R-HNLs which are preferably employed are R-HNLs from *Prunus amygdalys* (PaHNL), *Prunus domestica* (PdHNL) or from *Prunus serotina* (PsHNL).

Preferred recombinant R-HNLs are recombinant RHNLs from *Prunus domestica* (PdHNL), in particular PdHNL1, and the recombinant R-HNLs PaHNL1 to PaHNL5 which are described in EP 1223220, with particular preference for recombinant PaHNL5.

Suitable tunnel mutants are preferably native or recombinant R-HNLs in which preferably one bulky amino acid residue in the hydrophobic channel leading to the active center has been replaced by a less bulky amino acid residue such as, for example, alanine, glycine, valine or phenylalanine.

The R-HNLs to be modified may moreover be in the form of an altered sequence which is obtained for example by exchange of the first amino acid(s) in the sequence or by deletion of the first amino acid(s) or by attachment of further amino acids, such as, for example, GluAlaGluAla.

A further possibility before the mutation in the active center is to exchange the natural or vegetable signal sequence for another signal sequence such as, for example, for the signal sequence of the alpha mating factor from *Saccharomyces cerevisiae* (alpha-MF), *Saccharomyces cerevisiae* invertase (SUC2), Pichia*killer* toxin signal sequence, α-amylase,

*Pichia pastoris* acid phosphatase (PHO1), *Phaseolus vulgaris* agglutinin (PHA-E); glycoamylase signal sequence from *Aspergillus niger* (glaA), glucose oxidase (GOX) signal sequence from *Aspergillus niger*, Sec10 signal sequence from *Pichia pastoris*, signal sequence of the 28 kD subunit of the killer toxin from *Klyveromyces lactis*, BSA signal sequence, etc., or a recombinant signal sequence thereof. The signal sequences may moreover comprise point mutations.

Suitable signal sequences and their mutants are described for example in Heijne G. et al., FEBS Letters 244 (2), 439-46 (1989), EP 19911213, Paifer et al., Biotecnologia Aplicada 10(1), 41-46, (1993), Raemaekers et al., European Journal of Biochemistry 265(1), 394-403 (1999) etc.

The vegetable signal sequence is preferably replaced by the signal sequence of the alpha mating factor from *Saccharomyces cerevisiae*.

The R-HNLs of the invention are prepared by site-specific mutagenesis, for example using the Quick Change (XL) Site Directed Mutagenesis Kit, Quick Change Multi Site Directed Mutagenesis Kit (from Stratagene), and kits from Invitrogen or Promega etc. in accordance with the manufacturer's instructions or by other conventional methods as described for example in Current Protocols in Molecular Biology, Ausubel et al., 2003.

Site-directed mutagenesis kits are systems ready for use for preparing specific mutants and are sold commercially for example by Stratagene Cloning Systems, La Jolla, CA (USA).

In the site-specific mutagenesis, there is according to the invention replacement in the active center of the R-HNL either of
a) an alanine residue by glycine, valine, leucine, isoleucine or phenylalanine or
b) a phenylalanine residue by alanine, glycine, valine, leucine or isoleucine or
c) a leucine residue by alanine, glycine, valine, isoleucine or phenylalanine or
d) an isoleucine residue by alanine, glycine, valine, leucine or phenylalanine.

In the mutants resulting therefrom the abovementioned residues, which are located in the active center in the direct vicinity of the substrate-binding site, are exchanged.

It is preferred in this connection for there to be replacement either of an alanine residue by glycine, valine or leucine or of a phenylalanine residue by alanine, leucine or glycine or of a leucine residue by alanine, glycine or phenylalanine.

For conversion of large substrates such as, for example, of aromatic aldehydes or ketones having bulky radicals or with substituents in the ortho or meta position, or of bulky aliphatic aldehydes or ketones, preferably one of the amino acids alanine, valine, leucine, isoleucine or phenylalanine is replaced by a smaller amino acid residue in each case. Thus, for example, phenylalanine is replaced by leucine or alanine; or alanine by glycine etc.

For conversion of smaller substrates such as, for example, smaller aliphatic aldehydes or ketones, by contrast, preferably one of the amino acids alanine, valine, leucine, isoleucine or phenylalanine is replaced by a larger amino acid residue in each case, such as, for example, alanine by leucine or valine, or leucine by phenylalanine.

Particular preference is given to mutants of the recombinant R-hydroxynitrile lyases PaHNL1-PaHNL5 which are disclosed for example in EP 1223220 and which may optionally also have a mutation in the hydrophobic channel leading to the active center.

Especial preference is given to mutants of the recombinant R-hydroxynitrile lyase PaHNL5, which may optionally also have a mutation in the hydrophobic channel leading to the active center, in which there is replacement in the active center of
a) the alanine residue in position 111 by glycine, valine or leucine or
b) the phenylalanine residue at position 72 by alanine or leucine or
c) the leucine residue at position 331 or 343 by alanine or glycine.

The numberings are derived from the corresponding positions in the mature unmodified recombinant R-hydroxynitrile lyase PaHNL5, but the positions can be shifted according to the abovementioned modifications of the sequence, such as, for example, truncation or extension of the sequence.

Secretory expression in suitable microorganisms then takes place, such as, for example, in *Pichia pastoris*, *Saccharomyces cerevisiae* or *Escherichia coli*, *Bacillus subtilis*, *Klyveromyces lactis*, *Aspergillus niger*, *Penicillium chrysogenum*, *Pichia methanolica*, *Pichia polymorpha*, *Phichia anomala*, *Schizosaccharomyces pombe* etc.

The resulting R-HNL mutants of the invention are purified by standard methods, for example in analogy to Dreveny et al.; Structure (Cambridge; MA, United States) 9(9), 803-815; 2001.

The R-HNL mutants of the invention are suitable for the preparation of enantiopure R- or S-cyanohydrins in a conversion rate which is increased compared with the prior art, the R-HNL mutants of the invention also being distinguished by a high pH stability at low pH values.

The invention accordingly relates further to the use of the R-HNL mutants of the invention for preparing enantiopure R- or S-cyanohydrins.

The R-HNL mutants of the invention are employed in particular with aliphatic and aromatic aldehydes and ketones as substrates.

Aldehydes mean in this connection aliphatic, aromatic or heteroaromatic aldehydes. Aliphatic aldehydes mean in this connection saturated or unsaturated, aliphatic, straight-chain, branched or cyclic aldehydes. Preferred aliphatic aldehydes are straight-chain or branched aldehydes having in particular 2 to 30 C atoms, preferably of 4 to 18 C atoms, which are saturated or mono- or polyunsaturated. The aldehyde may in this connection have both C-C double bonds and C-C triple bonds. The aliphatic, aromatic or heteroaromatic aldehydes may moreover be unsubstituted or substituted by groups which are inert under the reaction conditions, for example by optionally substituted aryl or heteroaryl groups, such as phenyl, phenoxy or indolyl groups, by halogen, hydroxy, hydroxy-$C_1$-$C_5$-alkyl, $C_1$-$C_5$-alkoxy, $C_1$-$C_5$-alkylthio, ether, alcohol, carboxylic ester, nitro or azido groups.

Examples of preferred aliphatic aldehydes are butanal, 2-butenal, 3-phenylpropanal, hydroxypivalaldehyde etc. Examples of aromatic or heteroaromatic aldehydes are benzaldehyde and variously substituted benzaldehydes such as, for example, 2-chlorobenzaldehyde, 3-chlorobenzaldehyde, 4-chlorobenzaldehyde, 3,4-difluorobenzaldehyde, 3-phenoxybenzaldehyde, 4-fluoro-3-phenoxybenzaldehyde, hydroxybenzaldehydes, methoxybenzaldehydes, also furfural, methylfurfural, anthracene-9-carbaldehyde, furan-3-carbaldehyde, indole-3-carbaldehyde, naphthalene-1-carbaldehyde, phthalaldehyde, pyrazole-3-carbaldehyde, pyrrole-2-carbaldehyde, thiophene-2-carbaldehyde, isophthalaldehyde or pyridinealdehydes, thienylaldehydes etc.

Ketones are aliphatic, aromatic or heteroaromatic ketones in which the carbonylcarbon atom has different substituents. Aliphatic ketones mean saturated or unsaturated, straight-chain, branched or cyclic ketones. The ketones may be saturated or mono- or poly-unsaturated. They may be unsubstituted or substituted by groups which are inert under the reaction conditions, for example by optionally substituted aryl or heteroaryl groups such as phenyl or inolyl groups, by halogen, ether, alcohol, carboxylic ester, nitro or azido groups.

Examples of aromatic or heteroaromatic ketones are acetophenone, indolylacetone etc.

Aldehydes and ketones suitable according to the invention are known or can be prepared in a conventional way.

The substrates are converted in the presence of the HNLs of the invention with a cyanide group donor. Suitable as cyanide group donor are hydrocyanic acid, alkali metal cyanides or a cyanohydrin of the general formula I $$R_1R_2C(OH)(CN).$$

In formula I, $R_1$ and $R_2$ are independently of one another hydrogen or an unsubstituted hydrocarbon group, or $R_1$ and $R_2$ together are an alkylene group having 4 or 5 C atoms, with $R_1$ and $R_2$ not both being hydrogen. The hydrocarbon groups are aliphatic or aromatic, preferably aliphatic groups. $R_1$ and $R_2$ are preferably alkyl groups having 1-6 C atoms, and the cyanide group donor is very preferably acetone cyanohydrin.

The cyanide group donor can be prepared by known processes. Cyanohydrins, especially acetone cyanohydrin, can also be purchased.

The cyanide group donor employed is preferably hydrocyanic acid (HCN), KCN, NaCN, or acetone cyanohydrin, particularly preferably hydrocyanic acid. The hydrocyanic acid can moreover be liberated only shortly before the reaction from one of its salts such as, for example, NaCN or KCN and be added undiluted or in dissolved form to the reaction mixture.

The conversion can be carried out in an organic, aqueous or 2-phase system or in emulsion, and without diluent.

An aqueous solution or buffer solution comprising the HNL of the invention is used as aqueous system. Examples thereof are Na citrate buffer, phosphate buffer etc.

It is possible to use as organic diluent, water-immiscible or slightly water-miscible aliphatic or aromatic hydrocarbons, which are optionally halogenated, alcohols, ethers or esters or mixtures thereof or the substrate itself. Methyl tert-butyl ether (MTBE), diisopropyl ether, dibutyl ether and ethyl acetate or mixtures thereof are preferably employed.

The HNLs of the invention can moreover be present either as such or immobilized in the organic diluent, but the conversion can also take place in a two-phase system or in an emulsion with nonimmobilized HNL.

The conversion moreover takes place at temperatures of from −10° C. to +50° C., preferably at −5° C. to +45° C.

The pH of the reaction mixture can be from 1.8 to 7, preferably from 2 to 4 and particularly preferably from 2.5 to 3.5.

EXAMPLE 1

Figure 1:
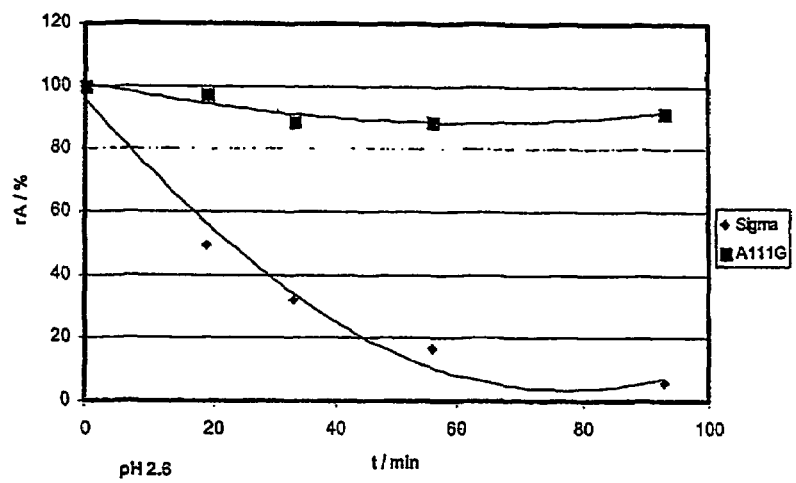
FIG. 1 shows pH stability of mutant PaHNL5 A11 G.

Cloning of the pahnl4 gene from *Prunus amygdalus*

Gene-specific PCR primers based on the sequence homology of the mdl4 gene of *Prunus serotina* were prepared:

The amplification took place in a 50 µl mixture with 1.2 U of "Hotstar" Taq DNA polymerase (Qiagen, Hilden, Germany), with 50 ng of genomic almond DNA (isolated from Farmgold almond kernels batch number L4532, 1999 harvest) as "template" and 10 pmol of each of the primers mandlp2f (oBT2204) and mandlp5r (oBT2206), 5 µl of DNTP (2 mM each) mix, all in 1× PCR buffer in accordance with the manual of the "Hotstar Kit" (Qiagen, Hilden, Germany), starting with a 15-minute denaturation step at 95 DEG C, followed by 10 cycles (1 min 94 DEG C, 1 min 45 DEG C; 1 min 72 DEG C) for preamplification, 20 further cycles (1 min 94 DEG C, 1 min 68 DEG C, 1 min 72 DEG C) for amplification of specific products and a final incubation at 72 DEG C for 5 min. A DNA fragment about 2.2 kb in size (determined by agarose gel electrophoresis analysis) was obtained in this PCR. This PCR product was purified from an agarose gel using the "Qiaquick Kit" (Qiagen, Hilden, Germany) in accordance with the manual included, cloned via the EcoRI cleavage sites into the pBSSK(−) cloning vector, and sequenced using the "Dye Deoxy Terminator Cycle Sequencing" kit (Applied Bio-systems Inc., Forster City, CA, USA) by the primer walking strategy. New PCR primers were derived from the 5' and 3' regions of the DNA sequence and employed for a new PCR. The reaction mixture chosen for this was as follows: 20 ng of genomic DNA, 10 pmol each of the two primers pamhnl4a (oBT2544) and pamhnl4e (oBT2543), 2 µl of dNTP mix (5 mM each), 1× Hotstar PCR buffer and 1.2 U of Hotstar DNA polymerase (Qiagen, Hilden, D). Amplification took place after a 15-minute step at 95 DEG C with 30 cycles (1 min 94 DEG C, 30 sec 60 DEG C, 2 min 72 DEG C) and 15 min at 72 DEG C. The PCR product was purified twice on Qiaquick (Qiagen, Hilden, D) columns and directly sequenced in order to avoid sequence errors in cloned PCR products. The exons were identified in the resulting DNA sequence of the PCR fragment which is a total of 2232 base pairs in length, and the protein sequence of the PaHNL4 isoenzyme was derived from the coding sequence.

```
oBT2204 mandlp2f:
5'-ACTACGAATTCGACCATGGAGAAATCAAC-3' oBT2206 mandlp5r:
5'-CACTGGAATTCAAAGAGCAACACTTATCCACGG-3' oBT2543 pamhnl4e:
5'-AAGAGGAACACTTAGCCACG-3' oBT2544 pamhnl4a:
5'-CAACAATGTCCGCTGTAGTG-3'
``` are listed as SEQ ID NOS:1-4 in the attached Sequence Listing.

EXAMPLE 2

Replacement of the Signal Sequence 2 variants were chosen as N terminus of the calculated mature protein (secreted protein after elimination of the signal peptide and of the additional GluAlaGluAla sequence) in order to avoid accumulation of incompletely processed enzyme in the interior of cells:

A) leucine as N-terminal amino acid as also occurs in the wild-type sequence and which is regarded, according to the N-end rule, as primary destabilizing amino acid (Varshavsky et al., Proceedings of the National Academy of Science of the United States of America, 93(22), 12142-12149, 1996).

B) glutamine (mutation L1Q) as N-terminal amino acid which is described as tertiary destabilizing amino acid (Varshavsky et al., 1996).

PCR I:

The signal sequence of the alpha mating factor of *Saccharomyces cerevisiae* was highly amplified from the template PPICZB (Invitrogen Inc, San Diego, Calif., Cat. No. V19520). The PCR primers were constructed so that the EcoRI cleavage site of the Invitrogen plasmid at the 3' end of the signal sequence was destroyed. This made it possible to clone the entire gene construct including the signal sequence via EcoRI cleavage sites into various Pichia expression vectors. The pairs of primers used for this purpose were alpha11/alpha21a and alpha11/alpha21aQ. The primers alpha11 and hnl5α21 comprise an EcoRI cleavage site. The primers alpha21a and alpha21aQ also comprised a DNA sequence region which codes for the 5' end of the mature PaHNL5 isoenzyme. The primer alpha21aQ comprised a sequence modification which leads to the mutation L1Q at the N terminus of the expected mature secreted protein. At the end of the alpha factor signal sequence there was a Kex2 cleavage site and a GluAlaGluAla sequence processed by Ste13.

The PCR was carried out in a 50 µl mixture (10 ng of template, 0.1 µM of each primer, 0.2 mM dNTPs, 5 µl of PCR buffer, 1 U of Pwo polymerase from Roche) in a thermocycler from Applied Biosystems (Forster City, Calif.). A denaturation step at 94° C. for 2 min was followed by amplification in 30 cycles (30 sec 94° C., 60 sec 62° C., 1 min 30 sec 72° C.) and a concluding step at 72° C. for 7 min.

PCR II:

The hnl5 gene was highly amplified from the plasmid pHILDPaHNL5a (BT4256) using the pairs of primers hnl5α11/hnl5α21 and hnl5α11Q/hnl5α21. The primers hnl5α11 and hnl5α11Q also comprised a DNA sequence region which corresponded to the 3' end of the fragment with the alpha factor signal sequence (see above). The primer hnl5α21 comprised an EcoRI cleavage site.

The PCR was carried out in a 50 µl mixture (10 ng of template, 0.1 µM of each primer, 0.2 mM dNTPs, 5 µl of PCR buffer, 1 U of Pwo polymerase from Roche) in a thermocycler from Applied Biosystems. A denaturation step at 94° C. for 2 min was followed by amplification in 30 cycles (30 sec 94° C., 60 sec 65° C., 3 min 30 sec 72° C.) and a concluding step at 72° C. for 7 min.

Overlap Extension:

3 µl of each of the products from PCR I and PCR II were employed as template and simultaneously as primers for completion to give a coherent product. Extension took place in a 45 µl mixture with 5 µl of Pwo PCR buffer, 0.2 mM dNTPs and 1 unit of Pwo polymerase (Roche, Mannheim, D). The mixture was heated at 94° C. for 2 min and then incubated in a thermocycler with 10 cycles at 94° C. for 30 sec and at 72° C. for 3 min.

PCR III:

The product from the overlap extension was amplified by using the primers alpha11 and hnl5α21. 5 µl of primer mix (3 µl of water and 1 µl of each of the primers alpha11 and hnl5α21, the concentration of the primers being 5 µM) were added to the overlap extension PCR mixture, and the product was amplified with 20 cycles (30 sec 94° C., 45 sec 62° C., 4 min 72° C.). Finally, incubation took place at 72° C. for 7 min. The PCR product was purified by the Qiaquick purification protocol of Qiagen (Hilden, D), cut with EcoRI and cloned into the vector pHILD2 (Invitrogen, San Diegeo, Calif).

Primer Sequences:

```
oBT2835 alpha11:
5'-tcttcgaagaattcacgATGAGATTTCCTTCAATTTTTACTGC-3' oBT2841 alpha21a:
5'-gaagtattggcaagAGCTTCAGCCTCTCTTTTCTCG-3' oBT2843 alpha21aQ:
5'-gaagtattggcttgAGCTTCAGCCTCTCTTTTCTCG-3' oBT2837 hnl5α11:
5'-agagaggctgaagctCTTGCCAATACTTCTGCTCATG-3' oBT2842 hnl5α11Q:
5'-agagaggctgaagctCAAGCCAATACTTCTGCTCATG-3' oBT2838 hnl5α21:
5'-atggtaccgaattcTCACATGGACTCTTGAATATTATGAATAG-3'
``` are listed as SEQ ID NOS:5-10 in the Sequence Listing.

Extensions are in lower case.

The resulting plasmids were called pHILDPaHNL5α (BT4338) and pHIL/PaHNL5α_L1Q (BT4339). Transformation into *Pichia pastoris* took place by the standard Invitrogen procedure.

Sterile toothpicks were used to inoculate deep well culture plates with in each case approximately 2000 transformants, which were cultured for the screening for active transformants.

EXAMPLE 3

Culturing of *Pichia pastoris* Transformants and production of PaHNL5 Variants a) Microcultures in Deep Well Plates 250 µl of BM0.5G medium (0.2 M potassium phosphate, pH 6.0; 13.4 g/l yeast nitrogen base, 5 g/l glycerol, 0.8 mg/l biotin) in 2 ml deep well plates were inoculated with single colonies of transformants and shaken at 28° C. and 340 rpm. Induction of expression via the AOX1 promoter took place by adding 250 µl of BMM2 medium (0.2 M potassium phosphate, pH 6.0; 13.4 g/l yeast nitrogen base, 20 ml/l methanol, 0.8 mg/l biotin) after 60-70 hours. Further methanol additions took place after 10, 24 and 48 hours by adding in each case 50 µl of BMM10 (0.2 M potassium phosphate, pH 6.0; 13.4 g/l yeast nitrogen base, 100 ml/l methanol, 0.8 mg/l biotin).

About 72 hours after the induction, the cells were spun down and the culture supernatant was employed directly, diluted, or concentrated by ultrafiltration through Vivaspin 30 kDa exclusion membranes from Sartorius (Göttingen, D) for measuring the enzymic activity.

b) "Scale Up" in Shaken Flasks 225 ml of BM0.5G medium (0.2 M potassium phosphate, pH 6.0; 13.4 g/l yeast nitrogen base, 5 g/l glycerol, 0.8 mg/l biotin) in 2 liter flasks with baffles were inoculated with a large single colony and shaken at 28° C. and 120 rpm. Induction of expression via the AOX1 promoter took place by adding 25 ml of BMM10 medium (0.2 M potassium phosphate, pH 6.0; 13.4 g/l yeast nitrogen base, 100 ml/l methanol, 0.8 mg/l biotin) after 60-70 hours. Further additions of 2.5 ml of methanol per shaken flask (250 ml) took place after 10, 24 and 48 hours.

About 72 hours after the induction, the cells were spun down and the culture supernatant was employed directly, diluted or concentrated by ultrafiltration through 30 kDa exclusion membranes for measuring the enzymic activity.

EXAMPLE 4

Site-Specific Mutagenesis 10 ng of the expression plasmid pHILDPaHNL5α_L1Q (PaHNL5 with alpha factor signal sequence) were employed as template for the mutagenesis reaction using the Quik Change XL Site Directed Mutagenesis Kit from Stratagene (Cat. #200516). 200 ng of each of the mutagenesis primers were employed for the reaction. The following temperature program was used:
A) denaturation at 95° C. for one minute
B) 18 cycles with 50 sec at 95° C., 50 sec at 60° C. and 20 min at 68° C.
C) extension for 7 min at 68° C.

The template DNA was digested off with DpnI, as described in the kit protocol, and 2 μl of the mixture were employed as described for transforming ultracompetent *E. coli* XL 10 gold cells. Plasmid DNA was prepared from the transformants and sequenced. Plasmids from mutants having the correct sequence in the region of the coding DNA insert were replicated and transformed into *Pichia pastoris* GS115 with the aid of the standard Invitrogen procedure.

Several hundred histidine-autotrophic *Pichia* transformants were cultivated as described above in deep well plates, and the activity of the culture supernatants was determined with racemic mandelonitrile in 96-well plates. Clones having in each case the highest enzymic activity of the individual mutants were selected for shaken flask experiments. The enzymic activity of the culture supernatants was determined using the substrate mandelonitrile (DSM Fine Chemicals Linz, A).

The following mutations were carried out:

A111, A111L, A111V, F72A, L331A and L343A, and as comparative experiment V317A and V317G PCR primers for the site-specific mutagenesis:

```
oBT2966  oPaHNL5A111Gf:
5'-GTGGCACGACCATAATCAATGGAGGCGTCTACGCCAGAGCTAAC-3' oBT2967  oPaHNL5A111Gr:
5'-GTTAGCTCTGGCGTAGACGCCTCCATTGATTATGGTCGTGCCAC-3' oBT3080  oPaHNL5A111Lf
5'  GCACGACCATAATCAATGCTTGCGTCTACGCCAGAGCTAAC  3' oBT3081  oPaHNL5A111Lr
5'  GTTAGCTCTGGCGTAGACGCAAGCATTGATTATGGTCGTGCCAC  3' oBT3078  oPaHNL5A111Vf
5'  GTGGCACGACCATAATCAATGGTTGCGTCTACGCCAGAGCTAAC  3'
```

-continued
```
oBT3079  oPaHNL5A111Vr
5'  GTTAGCTCTGGCGTAGACGCAACCATTGATTATGGTCGTGCCAC  3' oBT2983  oPaHNL5V317(A,G)f:
5'  TCCAATTGAAGCCTCTGTTGSAACTGTTTTAGGCATTAGAAGTG  3' oBT2984  oPaHNL5V317(A,G)r:
5'  CTAATGCCTAAAACAGTTSCAACAGAGGCTTCAATTGGATTTGG  3' oBT3017  oPaHNL5F72Af:
5'  CACGTTGACTGCAGATGGGGCTGCATATAATCTGCAGCAACAAG  3' oBT3018  oPaHNL5F72Ar:
5'  CTTGTTGCTGCAGATTATATGCAGCCCCATCTGCAGTCAACGTG  3' oBT3019  oPaHNL5L343Af:
5'  CCACTCCACCCTTTAGTGCTTTTCCTACAACATCTTACCCCCTC  3' oBT3020  oPaHNL5L343Ar:
5'  AAGATGTTGTAGGAAAAGCACTAAAGGGTGGAGTGGAAAATGGC  3' oBT3021  oPaHNL5L331Af:
5'  AGTGATTATTATCAAGTTTCTGCCTCAAGCTTGCCATTTTCCAC  3' oBT3022  oPaHNL5L331Ar:
5'  GGAAAATGGCAAGCTTGAGGCAGAAACTTGATAATAATCACTTC  3'
```

S=G or C are listed as SEQ ID NOS:11-24 in the Sequence Listing.

EXAMPLE 5

Check of Sequences by "Colony PCR"

To check whether a mistake has occurred during Pichia transformation or during selection of the strain, the integrated mutated HNL5 gene was amplified by PCR and sequenced in the region of the mutation which had been carried out.

For this purpose, a single colony was suspended with 0.5 ml of water and boiled at 95° C. for 30 min. This mixture was then centrifuged in a bench centrifuge at 13 500 rpm for 1 min. 5 μl of the supernatant were employed as template for the PCR amplification of the mutated hnl5 gene. The complete mixture with a volume of 50 μl comprised additionally 0.2 mM of each of the primers oBT2907 and oBT2908a, 0.2 mM dNTPs, 1× Hotstar (Qiagen) PCR buffer and 2.5 U of Hotstar DNA polymerase. The 3-stage PCR took place in the following steps:

Once at 95° C. for 15 min, then 30 cycles with 30 seconds at 94° C., 1 min at 55° C. and 2.5 min at 72° C. and finally once at 72° C. for 10 min.

3 μl of this PCR mixture were employed after the amplification as template for reamplification in order to obtain sufficient material for DNA sequencing. The reaction conditions were the same as for the first amplification. The PCR product from the reamplification was employed for the sequencing after purification twice by the Qiaquick method of Qiagen.

```
oBT2907:  5'-GCAAATGGCATTCTGACATCC-3' oBT2908a: 5'-GACTGGTTCCAATTGACAAGC-3'
``` are listed as SEQ ID NOS:25-26 in the Sequence Listing.

Transformants which expressed the PaHNL5 mutants were isolated, and the region of the mutation checked by sequencing by the colony PCR method.

Table 1 shows an overview of the respective expression strains of the mutants:

TABLE 1 modifications introduced into the pahnl5 gene

| Signal sequence | Pichia clone name | Pichia clone No. | Plasmid for Pichia transformation | AA exchange | DNA sequence |
|---|---|---|---|---|---|
| plant PaHNL5 signal | GS115pHILDPaHNL1a37 | BT2578 | BT4256 | | |
| Alpha factor | GS115pHILDPaHNL5alpha_G13 | BT2617 | BT4338 | | |
| Alpha factor | GS115pHILDPaHNL5alphaLIQ_H21 | BT2620 | BT4339 | LIQ | CTT→CAA |
| Alpha factor | GS115pHILDPaHNL5alpha_LIQ, A111G (= sp1a8F9) | BT2621 | BT4345 | LIQ<br>A111G | CTT→CAA<br>GCA→GGA |
| Alpha factor | GS115pHILDPaHNL5alpha_LIQ, V317A (= spA2.2) | BT2623 | BT4375 | LIQ<br>V317A | CTT→CAA<br>GTA→GCA |
| Alpha factor | GS115pHILDPaHNL5alpha_LIQ, V317G (= spAa) | BT2624 | BT4376 | LIQ<br>V317G | CTT→CAA<br>GTA→GGA |
| Alpha factor | GS115pHILDPaHNL5alpha_LIQ, F72A | BT2632 | BT4400 | LIQ<br>F72A | CTT→CAA<br>TTT→GCT |
| Alpha factor | GS115pHILDPaHNL5alpha_LIQ, L331A | BT2633 | BT4401 | LIQ<br>L331A | CTT→CAA<br>CTG→GCC |
| Alpha factor | GS115pHILDPaHNL5alpha_LIQ, L343A | BT2634 | BT4402 | LIQ<br>L343A | CTT→CAA<br>CTT→GCT |
| Alpha factor | GS115pHILDPaHNL5alpha_LIQ, F72A, L331A | BT2635 | BT4403 | LIQ<br>F72A<br>L331A | CTT→CAA<br>TTT→GCT<br>CTG→GCC |
| Alpha factor | GS115pHILDPaHNL5alpha_LIQ, F72A, L331A, L343A | BT2636 | BT4404 | LIQ<br>F72A<br>L331A<br>L343A | CTT→CAA<br>TTT→GCT<br>CTG→GCC<br>CTT→GCT |
| Alpha factor | GS115pHILDPaHNL5alpha_LIQ, A111L | BT2637 | BT4405 | LIQ<br>A111L | CTT→CAA<br>GCA→CTA |
| Alpha factor | GS115pHILDPaHNL5alpha_LIQ, A111V | BT2638 | BT4406 | LIQ<br>A111V | CTT→CAA<br>GCA→GTT |

EXAMPLE 6

Purification and Characterization of *Prunus amygdalus* Enzyme Variants

The specific activity of the respective mutants with different substrates was determined by carrying out several shaken flask cultures with each of the expression clones. The culture supernatant was concentrated by ultrafiltration (30 kDa cut-off) using 20 ml Vivaspin PES centrifugation columns from Sartorius (Gottingen, D) and then purified by chromatography.

Before the purification, the concentrated culture supernatant was equilibrated with the low-salt binding buffer A by repeated dilution and concentration with binding buffer A (20 mM citrate-phosphate buffer, pH 5.5) in 30 kDa ultrafiltration centrifugation modules (Vivaspin, Sartorius), and then purified on a Q-Sepharose Fast Flow (QFF) anion exchange column with a column volume of 10 ml in an AKTApurifier 10 FPLC system from Amersham Biosciences UK Limited (Buckinghamshire, GB). Elution took place with elution buffer B (20 mM citrate-phosphate buffer+1M NaCl, pH 5.5), using the following gradient profile for the different variants of PaHNL5 from heterologous production with *Pichia pastoris*:

One column volume as washing step proved to be ideal for washing out all unbound protein constituents. The concentration of buffer B (elution buffer: 20 mM citrate-phosphate buffer, 1M NaCl, pH 5.5) was raised in half a column volume to 4% and subsequently increased to 48% in a further column volume. The next step was to increase the concentration of elution buffer B to 70%, using 1½ column volume in this case.

Finally, the concentration was raised to the maximum of 100% in one column volume and was in conclusion left thereat for a further column volume (washing step without fractionation).

Those fractions which ought, according to evaluation of the chromatogram, to contain protein (depending on the peak position) underwent determination of the protein content using the Biorad (Hercules, Calif.) protein assay (Bradford method) and of the enzymatic activity using the substrate mandelonitrile. The 2-3 fractions with the highest activity were pooled and employed for analyzing the enzyme characteristics. The protein concentration was carried out with a Biorad (Hercules, Calif.) protein assay (Bradford). The standard used for producing a calibration line was native PaHNL from Sigma (M-6782 Lot 41H4016).

The culture supernatants were concentrated ~20-fold by cross-flow filtration and then purified by chromatography. Samples were taken of the purified enzymes and loaded directly onto a gel (protein gel NuPAGE 4-12% bis gel 1 mm×17 well; Invitrogen), or ~500 ng were deglycosylated with endoglycosidase H (#P0702L, NEB) (according to the procedure supplied) and then loaded. The standard used was "SeeBlue Plus2 Pre-Stained Standard" from Invitrogen (Carlsbad, USA).

To compare the substrate specificities, the protein concentration of the purified enzymes and the protein content in the culture supernatant was measured using the Biorad protein assay (Hercules, Calif.), and the specific activities were compared with racemic mandelonitrile photometrically and with 2-, 3- and 4-chlorobenzaldehyde by GC:

For this purpose, 15 mmol of substrate were dissolved in 2.1 ml of tert-butyl methyl ether (MTBE). 0.25 mg of the appropriate PaHNL was diluted with 50 mM K2HPO4/citrate buffer of pH 3.4 to a final volume of 3.7 ml, the buffer was again adjusted to pH 3.4 and then mixed with the substrate in MTBE in 20 ml glass vials. The solution was cooled to 10° C., and 1.2 ml of HCN was added with a syringe and stirred at 10° C. on a magnetic stirrer to form an emulsion. Samples were taken at various times, derivatized with acetic anhydride in the presence of pyridine and dichloromethane, and analyzed by GC on a cyclodextrin column (CP-Chirasil-Dex CB) or by HPLC.

TABLE 2

| | specific activities ($\mu$mol/min/mg) | | | |
|---|---|---|---|---|
| Mutant | Mandelonitrile (cleavage) | 2-Cl-benzaldehyde | 3-Cl-benzaldehyde | 4-Cl-benzaldehyde |
| WT | 295 +/− 30 | n.d. | n.d. | n.d. |
| AlphaWT | 325 +/− 30 | 92 +/− 30 | 260 +/− 120 | 514 +/− 80 |
| A111G | 8 +/− 3 | 402 +/− 90 | 482 +/− 60 | 458 +/− 50 |
| V317G | 6 +/− 1.5 | <10 (racemic) | 226 +/− 40 | 21 +/− 10 | n.d not determined
WT: PaHNL5 expressed with native vegetable signal sequence
AlphaWT: PaHNL5 with S. cerevisiae alpha mating factor preproleader, EAEA sequence and L1Q mutation
A111G: as AlphaWT with additional A111G mutation
V317G: as AlphaWT with additional V317G mutation (comparative experiment)

The measurements revealed that the specific activity of the A111G mutant with the substrate (R)-2-chloro-mandelonitrile was about 3-5 times higher than that for the recombinant wildtype WT and AlphaWT isoenzymes of PaHNL5. The activity with 3-chlorobenzaldehyde was also higher with the A111G mutant than with AlphaWT.

EXAMPLE 7

Preparation of Mutants A111G

A sufficient amount of enzyme for pilot conversions was prepared from the improved clone Pichia pastoris GS115 pHILDPaHNL5alpha_L1Q,A111G (=BT2621) in a pilot fermentation.

8 flasks (2 l wide-neck) with baffles, each containing 250 ml of BMG medium (according to the standard Invitrogen protocol), were inoculated with single colonies of the strain Pichia pastoris GS115pHILDPaHNL5alpha_$L_1$Q,$A_{111}$G and shaken (120 rpm) at 28° C. for 36 hours. Chemicals 1-9, quantities for 20 liters, were brought to a total weight of 15 kg with deionized water and introduced into a 40 l bioreactor (MBR, Oftringen, CH). Sterilization in situ was followed by adjustment of the pH of the medium to pH 5.0 with 28% ammonia through a sterile feed pump. 200 ml of sterile-filtered "trace element solution" (together with vitamin H-biotin) were then introduced through a feed bottle into the bioreactor. A further 200 ml of the "trace element solution" were also added every second day until the end of the fermentation. Inoculation took place with 1.4 kg of preculture from the shaken flasks. The initial weight of the fermenter contents was about 15 kg. With an operating temperature of 28° C., an aeration rate of 10-30 liters of air/min and a stirring speed between 350 and 700 rpm, the partial pressure of oxygen (pO2) was kept at a value >10% of the saturation concentration. After 27 hours, the biomass had grown to a value of 122.8 g/l wet weight of cells or 30 g/l cell dry weight (CDW). From this time onwards, about 70 g of sterile glycerol was added in small portions per hour. In this linear phase of growth it was possible to reach a biomass concentration in the region of 100 g/l CDW in a period of 60 hours.

Thereafter the third phase was initiated by inducing expression by adding methanol. The methanol content in the culture broth was in this case adjusted to a value of 0.8-1% by weight. As the oxygen consumption increased during the fermentation, methanol (0.8-1 percent by weight) was added anew in each case. The increase in the enzymatic activity was followed by photometric determination of the activity in the culture supernatant of samples which were taken approximately every 12 hours from the fermenter. After methanol induction for 210 hours, the increase in enzymic activity was very small and the cells were harvested by centrifugation at 4000 g for 20 min twice, and the culture supernatant was collected. The enzymic activity in the culture supernatant after centrifugation was 3.3 U/ml (standard HNL assay with rac. mandelonitrile), resulting in an enzyme yield of about 22 000 U for an overall yield of about 6.5 liters of culture supernatant from 14.3 kg of fermenter contents.

The supernatant was purified from remaining cell material by 0.2 u crossflow filtration (VIVASCIENCE Vivaflow 50 from Sartorius, Gottingen, D). Concentration took place by crossflow ultrafiltration with Sartorius 30 kDa 50 cm2 cutoff modules. Enzyme preparations with 24.5 U/ml and 57 U/ml were prepared in this way for pilot experiments on cyanohydrin synthesis. Since Pichia pastoris secretes scarcely any of its own proteins into the culture supernatant, the enzyme produced and concentrated in this way was also very pure by comparison with plant enzyme preparations.

The following chemicals were used to prepare the culture medium (amount per liter):

| | |
|---|---|
| 1. 85% ortho-phosphoric acid | 35 ml |
| 2. CaSO$_4$ | 0.68 g |
| 3. K$_2$SO$_4$ | 18.8 g |
| 4. MgSO$_4$•7H$_2$O | 13.4 g |
| 5. KOH | 5.7 g |

(Chemicals 1 to 5 in analytical quality)

6. Glycerol, technical quality. 50 ml
7. Deionized water, conductivity 5.5-9.1 μS/cm
8. Antifoam 10% Acepol 83E (Carl Becker Chemie GmbH, Hamburg, D) 1 ml
9. 25% ammonia, technical quality 70 g/l Trace elements and vitamin H (all chemicals in analytical quality):

| | |
|---|---|
| 10. Biotin | 0.8 mg |
| 11. $CuSO_4 \cdot 5H_2O$ | 24.0 mg |
| 12. KI | 0.32 mg |
| 13. $MnSO_4 \cdot H_2O$ | 12.0 mg |
| 14. $Na_2MoO_4 \cdot 2\ H_2O$ | 0.2 mg |
| 15. $H_3BO_3$ | 0.08 mg |
| 16. $CoCl_2$ | 2.0 mg |
| 17. $ZnSO_4 \cdot 7H_2O$ | 80 mg |
| 18. $Fe(II)SO_4 \cdot 7H_2O$ | 260 mg |

EXAMPLE 8

Preparative Conversions with Benzaldehyde and 2-chlorobenzaldehyde

The enzyme properties in preparative synthesis were analyzed by converting 150 mmol of substrate in a reactor.

150 mM substrate were diluted or dissolved with 21 ml of MTBE. 5 mg of "PaHNL5alpha_L1Q,A111G" enzyme (A111G mutant) were diluted with 50 mM K2HPO4/citrate, pH 3.4, to a volume of 37.5 ml and adjusted to pH 3.4 with 10% strength citric acid. This aqueous phase was added to the organic phase and stirred in a 100 ml Schmizo KPG stirrer for 5 min. The temperature was kept at 10° C., and HCN was metered in by means of a perfuser pump for 1 hour. The reaction was stirred at 900 rpm at 10° C. For workup, the reaction solution was diluted with 140 ml of MTBE, stirred for 5 min and, after 10 min, the phases were separated. The aqueous phase was extracted once more with 40 ml of MTBE. After spontaneous phase separation, the organic phases were combined, stabilized with citric acid and evaporated. Analysis by GC was carried out as described above.

The conversions gave after 7 hours a yield of 95.1% 2-chlorobenzaldehyde cyanohydrin with an ee of 95.7% and a yield of more than 99% mandelonitrile with an ee of >99%.

EXAMPLE 9

Enzyme Stability at Low pH

The enzyme samples of commercially available native PaHNL from almond kernels (Sigma) and the A111G mutants were diluted in 50 mM citrate-phosphate buffer of pH 6.5 until, after a further 1:70 dilution, an increase of about 100 mOD was to be expected in the photometric determination of activity at 280 nm by the standard HNL assay with racemic mandelonitrile. 150 µl of these dilutions were transferred into 900 µl of 0.1M phosphate buffer with appropriately adjusted pH (dilution 1:7) and then, at various times after incubation at 22° C., 100 µl of these dilutions were employed for the determination of activity (100 µl of enzyme solution, 700 µl of 1M phosphate-citrate buffer of pH 5.0 and 200 µl of 60 mM mandelonitrile in 3 mM citrate-phosphate buffer of pH 3.5). The pH stability of the mutant PaHNL5 alpha_L1Q, A111G (A111G) at pH 2.6 compared with commercially available native PaHNL from almond kernels (Sigma) is evident from FIG. 1.

BRIEF DESCRIPTION OF DRAWINGS

FIG. 1 shows pH stability of mutant PaHNL5 Al 11G.

The invention claimed is:

1. An R-hydroxynitrile (R-HNL) lyase comprising the amino acid sequence of SEQ ID NO: 27.

2. A process for preparing enantiopure R-cyanohydrin comprising:
   (a) contacting a substrate in the presence of a cyanide ion with the R-hydroxynitrile lyase of claim 1 in a reaction mixture, and
   (b) recovering enantiopure R-cyanohydrin from the reaction mixture.

3. A process for preparing enantiopure R-cyanohydrins comprising contacting aliphatic, aromatic or heteroaromatic aldehydes or ketones in the presence of a cyanide ion with the R-hydroxynitrile lyase of claim 1 at a pH from 1.8 to 7.

4. The R-hydroxynitrile lyase of claim 1 which is obtained by expressing the nucleic acid encoding the R-hydroxynitrile lyase of claim 1 in a microorganism.

5. The R-hydroxynitrile lyase of claim 4, wherein said recombinant R-hydroxynitrile lyase is produced in a microorganism selected from the group consisting of *Pichia pastoris*, *Saccharomyces cerevisiae*, *Escherichia coli*, *Bacillus subtilis*, *Kluyveromyces lactis*, *Aspergillus niger*, *Penicillium chrysogenum*, *Pichia methanolica*, *Pichia polymorpha*, *Pichia anomala*, and *Schizosaccharomyces pombe*.

6. The R-hydroxynitrile lyase of claim 1 which is obtained by site-specific mutagenesis.

7. A process for preparing enantiopure R-cyanohydrin comprising contacting 2-chlorobenzaldehyde or 3-chlorobenzaldehyde in the presence of a cyanide ion with the R-hydroxynitrile lyase of claim 1 at a pH from 1.8 to 7.

8. The process according to claim 2 wherein said contacting occurs at a temperature from −5° C. to +45° C.

9. The process according to claim 7 wherein said contacting occurs at a temperature from −5° C. to +45° C.

* * * * *